United States Patent [19]

Nair et al.

[11] Patent Number: 5,429,826
[45] Date of Patent: Jul. 4, 1995

[54] CHEMICALLY FIXED MICELLES

[75] Inventors: Mridula Nair, Penfield, N.Y.;
Youngtai Yoo, Seoul, Rep. of Korea

[73] Assignee: Eastman Kodak Company, Rochester, N.Y.

[21] Appl. No.: 138,871

[22] Filed: Oct. 18, 1993

Related U.S. Application Data

[63] Continuation of Ser. No. 824,418, Jan. 23, 1992, abandoned.

[51] Int. Cl.$^6$ ............ A61K 47/34; A61K 9/133; C08G 81/00
[52] U.S. Cl. .................. 424/501; 424/426; 424/450; 525/901; 525/937; 525/938; 525/941; 514/772.1
[58] Field of Search ........... 424/426, 78.08, 78.17, 424/450, 409, 501; 525/430, 936, 938, 941, 901, 902; 523/201

[56] References Cited

U.S. PATENT DOCUMENTS

| | | | |
|---|---|---|---|
| 4,179,304 | 3/1978 | Kiovsky | 252/56 R |
| 4,997,772 | 3/1991 | Sutton et al. | 525/902 |
| 5,078,994 | 1/1992 | Nair et al. | 424/501 |
| 5,145,518 | 9/1992 | Winnik et al. | 106/21 |

FOREIGN PATENT DOCUMENTS

| | | | |
|---|---|---|---|
| 0291761 | 5/1988 | European Pat. Off. | C08G 63/08 |
| 2240547 | 8/1991 | United Kingdom | C08F 8/00 |

OTHER PUBLICATIONS

"Polymer Micelles As Novel Drug Carrier: Adriamycin-Conjugated Poly(ethylene Glycol)-Poly(Aspartic Acid) Block Copolymer" By Yokoyama et al, *Journal Of Controlled Release*, 11 (1990) Jan., Nos. 1/3, pp. 269–278.

"Lipid-Absorbing Polymers" by H. E. Marsh, Jr. & C. J. Wallace, *JPL Quarterly Technical Review*, vol. 2, No. 4, Jan. 1973, pp. 1–6.

"New Macromolecular Carriers For Drugs. I. Preparation and Characterization of Poly (oxyethylene-b-isoprene-b-oxyethylene) Block Copolymer Aggregates" by A. Rolland et al, *Journal of Applied Polymer Science*, Mar. 5, vol. 7, 44(1992) pp. 1195–1203.

"Photochemical Stabilization of Block Copolymer Micelles" by D. J. Wilson and G. Riess, *European Polymer Journal*, vol. 24, No. 7, pp. 617–621.

Park et al, *Synthesis of Microphased Core-Corona Type Microgel*, Polymer Communications, vol. 29 pp. 230–231 (1988).

Ishizu and Fukutomi, *Core-Shell Type Polymer Microspheres Prepared from Block Copolymers*, J. Polymer Sci., Part C: Polymer Letters, vol. 26, 281–286 (1988).

*Primary Examiner*—Edward J. Webman
*Attorney, Agent, or Firm*—Andrew J. Anderson

[57] ABSTRACT

There is provided copolymer particles wherein the particles are derived from chemically fixed micelles that comprise a copolymer. The copolymer is an amphiphilic block or graft copolymer comprising a water soluble component and an oleophilic component that can be crosslinked in an aqueous environment; and the oleophilic component is crosslinked. The particles can be dispersed in an aqueous continuous phase. The particles can contain other materials associated with the oleophilic component such as biochemical agents or other materials such as photographic materials such as couplers and dyes.

15 Claims, No Drawings

CHEMICALLY FIXED MICELLES

This is a continuation of application Ser. No. 824,418, filed 23 Jan. 1992, now abandoned.

FIELD OF THE INVENTION

The present invention is directed to copolymer particles, and aqueous compositions that include the particles, wherein the particles are derived from chemically fixed micelles that comprise a copolymer. These particles are useful as themselves as for example, impact modifiers or rheology control modifiers for polymers, or they can be used to carry other components such as photographically useful materials or biomedical agents.

BACKGROUND OF THE INVENTION

A characteristic feature of AB or ABA type block copolymers in solution is that they form sperical micelles in selective solvents which are thermodynamically good solvents for one block and poor solvents for the other. The free energy of the system is lowered in such solvents by micellar association compared to dispersed single chains. These micelles are made up of a compact core of the insoluble block with a soluble corona consisting of the second block. Since the association process is an equilibrium between micelles and free polymer (unimer), micellar stability can be influenced by the environment. Chemically fixing the core of the micelle could then render stability to the micellar aggregates.

It is known in the art to form a composition having a continuous organic phase having therein a copolymer micelle. The core is comprised of a less soluble or insoluble component of the block or graft copolymer and the shell or "corona" is formed of the organic solvent soluble component. It is also known to fix the insoluble core of the micelle by crosslinking. Reference is made to Park et al, *Synthesis of Microphased Core-Corona Type Microgel*, POLYMER COMMUNICATIONS, Vol 29 pg 230–231 (1988) and Ishizu and Fukutomi, *Core-Shell Type Polymer Microspheres Prepared from Block Copolymers*, J. Polymer Sci., Part C: Polymer Letters, Vol 26, 281–286 (1988). Such crosslinked micelles have not been isolated and no uses of the resulting particles are mentioned in these references.

No compositions are known of the general type described above where the continuous phase is water and the core of the micelle is a chemically fixed oleophilic component of the copolymer. That an oleophilic component can be identified, which is conveniently fixed in an aqueous medium, in the absence of surfactants, is not apparent.

It would be desirable to be able to form water based compositions since organic solvents often have adverse environmental impact. A further problem to be solved is to provide a composition that can carry in an aqueous medium, and possibly deliver in a controlled manner, hydrophobic materials such as photographically useful materials and biological agents.

SUMMARY OF THE INVENTION

In accordance with the present invention there are provided copolymer micellar particles wherein
a) the copolymer forming the micelle is an amphiphilic block or graft copolymer comprising a water soluble component and an oleophilic component that can be crosslinked in an aqueous environment; and
b) wherein the oleophilic component is crosslinked.

In accordance with another aspect of the present invention there is provided a composition comprising a continuous phase having therein chemically fixed micelles composed of a copolymer. The composition is characterized in that:
a) the continuous phase is aqueous;
b) the copolymer forming the micelle is an amphiphilic block or graft copolymer comprising a water soluble component and an oleophilic component that can be crosslinked in an aqueous environment; and
c) wherein the oleophilic component is crosslinked.

DETAILED DESCRIPTION OF THE INVENTION

The amphiphilic copolymers that are useful in the present invention have a water soluble component and an oleophilic component that is crosslinkable in an aqueous environment. One presently preferred class of polymeric components that is useful for the water soluble component in this invention is poly(alkylene oxides) such as poly(ethylene oxide). The term poly(alkylene oxides) as used herein includes polymers derived from alkylene oxides such as poly(ethylene oxides) and poly(proplyene oxides) including mixtures of ethylene and propylene oxides. The most preferred is poly(ethylene oxide).

Poly(ethylene oxides) are well known in the art and are described, for example, in U.S. Pat. No. 3,312,753 at column 4. Useful poly (alkylene oxide) block contains a series of interconnected ethyleneoxy units can be represented by the formula:

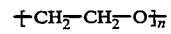

wherein the oxy group of one unit is connected to an ethylene group of an adjacent ethyleneoxy unit of the series.

Other useful water soluble components include poly (2-ethyloxazolines), poly (saccharides) and dextrans.

The oleophilic component of the polymers useful in the present invention can also be selected from many common components. The oleophilic component is characterized in that it is chemically crosslinkable in an aqueous environment either alone or through chemical modification of available functional groups. Exemplary oleophilic components can be derived from monomers such as: caprolactone; propiolactone; β-butyrolactone; δ-valerolactone; ε-caprolactam; lactic acid; glycolic acid; hydroxybutyric acid; lysine and its derivatives; and glutamic acid and its derivatives. Copolymer components, where the above monomers are functionalized with multifuctional monomers resulting in pendant crosslinkable groups, are also useful. Useful multifunctional monomers include: allyl glycidyl ether; glycidyl methacrylate; and poly(cyanoacrylate). Other useful oleophilic components can be derived from α,β-ethylenically unsaturated monomers, such as styrenics and acrylates, containing crosslinkable groups such as hydroxy, thiol, amine, chloromethyl and vinyl.

Where the composition of the invention contains a biomedical agent, and is intended to be injectable, it is desirable that the components of the copolymer be biocompatible and preferably also biodegradable.

Particularly preferred components of the block or graft copolymer useful in this invention are biodegradable polymers such as certain polyesters, polycarbonates, or polyamides. More particularly preferred polyesters include poly-(caprolactone) and its derivatives, poly (lactic acid), poly (3-hydroxybutyrate-co-3-hydroxyvalerate, poly (3-hydroxybutyrate) and poly(glycolic acid).

Biocompatible means that the material must be blood compatible and does not cause an adverse reaction in the body. For example, to be biocompatible, the material should not be toxic, immunogenic or thrombogenic. Biodegradable means that the material can be degraded either enzymatically or hydrolyrically under physiological conditions to smaller molecules that can be eliminated from the body through normal processes.

Where at least one of the components of the copolymer are biodegradable, the compositions can provide for controlled release of a material associated with the chemically fixed micelle. For example, a drug can be associated with the crosslinked oleophilic core of the chemically fixed micelle. Enzymatic degradation, such as by a hydrolase, of the core can release the drug over a period of time.

The copolymers can be either block or graft copolymers. Block copolymers can be of the "A-B" type where A represents the water soluble component and B represents the oleophilic component or of the A-B-A type. The typical graft copolymer is of the basic structure:

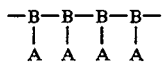

although graft and random graft copolymers of the following structures are also contemplated:

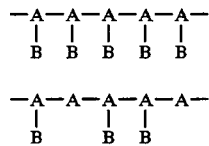

The molecular weights of the water soluble component and the oleophilic component are not critical. A useful range for the molecular weight of the water soluble component is between about 1,000 and 50,000, and preferably 2,000 and 15,000. The molecular weight of the oleophilic component is between about 300 and 25,000 and preferably between 1,000 and 10,000.

The oleophilic component can be crosslinked using a variety of methods depending on the specific component. Where the oleophilic component has pendant crosslinkable groups such as acrylate, methacrylate or vinyl, resulting from copolymerization of caprolactone with multifunctional monomers such as glycidyl methacrylate, the oleophilic component can be crosslinked using an initiator and heat or light. Where the oleophilic ends in a hydroxy group, such as polymerized caprolactone, the oleophilic component can be crosslinked by heating above its melting point in the presence of a free radical initiator or by γ irradiation or can be modified to facilitate crosslinking by the termination of the component with a crosslinkable group (endcapping). Useful crosslinking groups, for example, include unsaturated groups such as acrylates or maleares or alkoxy silane groups. Optionally, auxiliary crosslinking agents, such as polyfunctional acrylates or styrenics, polyfunctional aziridenes or polyfunctional epoxides may be included in the micellar core during crosslinking.

Crosslinking of the oleophilic component in the core increases the stability of the chemically fixed micelies. The chemically fixed micelles are considered to be stable if the crosslinked micelles with water as the continuous phase, are stable (do not dissolve) when the composition is mixed with three times as much of a good solvent for both blocks, such as acetone, as there is water. Crosslinking can also be confirmed by thermal analysis. The glass transition temperature of the oleophilic component will be increased and its heat of fusion decreased by crosslinking.

The crosslinked oleophilic center or core of the chemically fixed micelle can have associated therewith a variety of useful materials. Materials such as photographically useful materials, such as dyes, antifogging agents, antistatic agents and like can be incorporated. Biologically useful materials can also be incorporated.

Biomedical agents such as therapeutic agents, diagnostic agents, dyes or contrast agents, can be included in the core of the chemically fixed micelle. The term biomedical agent as used herein includes biologically active substances which are effective in the treatment of a physiological disorder, pharmaceuticals, enzymes, hormones, steroids, recombinant products and the like. Exemplary therapeutic agents are antibiotics, thrombolytic enzymes such as urokinase or streptokinase, insulin, growth hormone, chemotherapeutics such as adriamycin and antiviral agents such as interferon and acyclovir.

The term "diagnostic agent" as used herein includes materials which can act as contrast agents and thereby produce a detectable indicating signal in the host mammal. The detectable indicating signal may be gamma-emitting, radioactive, echogenic, fluoroscopic or physiological and the like.

In addition to biomedical agents, other materials can be associated with the oleophilic core of the chemically fixed micelle. Other useful materials include, for example, photographically useful materials such as couplers and dyes.

The biomedical agent or other useful material is associated with the chemically fixed micelle. By associated with, it is meant that the agent is carried by the chemically fixed micelle, particularly the core of the chemically fixed micelle. It could be dissolved in the oleophilic component of the core, covalently attached to the core or in the form of fine dispersion in the core.

Where the chemically fixed micelles contain biologically useful materials, they can be used in injectable compositions. For this purpose, the size should be between about 10 run and 1,000 nm, preferably between 20 nm and 300 run. In other applications, the dimensions of the chemically fixed micelles can vary over a very wide range.

Representative Preparation of Useful Copolymers

α-Methyl-ω-hydroxy poly(ethylene oxides) [CH$_3$PEOH, M.W.=2000 & 5000 g/mole] were obtained from Sigma and Aldrich and purified by dissolution in toluene and precipitation using methanol. They were subsequently dried under reduced pressure.

ε-Caprolactone (CL) was obtained from Aldrich and purified by distillation under reduced pressure over calcium hydride.

Isocyanatoethyl methacrylate was obtained from Polysciences and used as received.

Glycidyl methacrylate was also purchased from Polysciences and was distilled under reduced pressure before use.

I. Synthesis of α-Methyl-poly(ethylene oxide-b-caprolactone) [PEO-b-PCL 5K-5K] via ring opening polymerization.

CH₃PEOH (5K,10 gm) was degassed and dried under reduced pressure at 100° C. in a 2-neck round bottom flask for one hour. It was then dissolved at room temperature in toluene (50 ml, distilled over calcium hydride) under argon to give a 20% solution of the polymer and subsequently treated with 0.2–0.3 ml stannous octanoate (catalyst, 0.1–0.5 wt % with respect to CH₃PEOH and ε-caprolactone combined). The appropriate amount of ε-caprolactone (10 ml) was introduced into the reaction mixture using a syringe and polymerized at 100°–110° C. for 16–20 hrs. The polymer solution was then precipitated into large amounts of diethyl ether and filtered. (Similar copolymers were precipitated into either diethyl ether or methanol.) Proton NMR showed peaks at 3.61 ppm corresponding to the methylene groups of the polyethylene oxide segment of the polymer and peaks at 1.4, 1.6, 2.3, and 4.1 ppm corresponding to the methylene groups of the polycaprolactone segment of the polymer. Gel permeation chromatography was used to determine molecular weight distributions.

II. Functionalizatin of α-methyl-poly(ethylene oxide-b-caprolactone) with methacrylate groups The polymerization reaction mixture from I after heating at 100° C. for 16–20 hrs. was treated with isocyanatoethylmethacrylate, 5% with respect to ε-caprolactone and the mixture stirred overnight at 55°–60° C. The product was isolated as usual by precipitation into ether. FTIR was used to confirm the incorporation of the methacrylate group.

III. Synthesis of poly(ethylene oxide-b-caprolactone) [2K-2K] via ring opening polymerization CH₃PEOH (2K, 5 gm) was placed in a pressure bottle equipped with a pressure gauge, vacuum outlet, and septum capped inlet tube. The polymer was degassed and dried under reduced pressure at 80° C. for one hour and then cooled to room temperature. Toluene (distilled over calcium hydride) was introduced into the bottle (25 ml) using a transfer needle followed by a stoichiometric amount of n-butyl lithium (0.63 ml, 1.6M in hexane) (triethyl aluminum (0.33 ml, 1M in heptane) can also be used). The temperature was raised to 80° C. for 5–15 hrs. releasing the pressure valve occasionally. ε-Caprolactone (5 ml) was introduced into the reactor using a syringe and continued stirring at 100° C. 16 hrs. After polymerization the product was isolated by precipitation into excess ether.

IV. Synthesis of poly(ethylene oxide-b-caprolactone) [5K—5K] containing randomly distributed methacrylate groups CH₃PEOH (5K, 5 gm) was placed in a pressure bottle equipped with a pressure gauge, vacuum outlet, and septum capped inlet tube. The poller was degassed and dried under reduced pressure at 100° C. for one hour and then cooled to room temperature. Toluene (distilled over calcium hydride) was introduced into the bottle (25 ml) using a transfer needle followed by a stoichiometric amount of n-butyl lithium (0.63 ml, 1.6M in hexane). The temperature was raised to 80° C. for 5–15 hrs. releasing the pressure valve occasionally. ε-Caprolactone (5 ml) and glycidyl methacrylate (1 ml) were introduced into the reactor using syringes and continued stirring at 100° C. 16 hrs. After polymerization the product was isolated by precipitation into excess ether as in Preparation I. Proton NMR showed peaks at 5.6 and 6.15 ppm corresponding to the pendant methacrylate groups in addition to the signals for CH₃PEOH and caprolactone.

In a similar manner, copolymers containing allyl glycidyl ether pendant groups were prepared by adding allyl glycidyl ether at the same time as the ε-caprolactone.

V. Micellar aggregates of PEO-b-PCL

The block copolymer prepared above in step IV (1 gm) was dissolved in a large excess of acetone (300 ml) and 100 ml distilled water was added slowly to the solution with stirring. The acetone was removed under reduced pressure and a bluish solution of the micelles in water was obtained. To exhaustively remove the acetone, the micellar solution was dialyzed using 50K molecular weight cut-off bags for 16 hours. Gas chromatography showed no acetone at this point. The micellar solution was then filtered through a series of filters (5 micron down to 0.2 micron).

VI. Preparation of Polyfunctional Crosslinkers

Preparation A.

Poly(ε-caprolactone) triol (M.W.=300, 5.1 g) was dried under reduced pressure at 70° C. for 2 hours. It was brought to room temperature, dissolved in dry tetrahydrofuran (10 ml) and treated with isocyanatoethyl methacrylate (7.9 g). The mixture was heated at 40° C. overnight and precipitated into petroleum ether. The product was isolated as a powder.

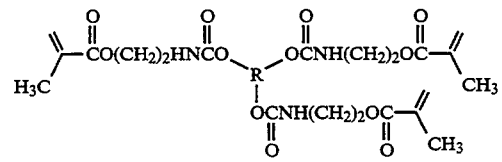

where R is poly(ε-caprolactone) triol

Preparation B

Poly(ε-caprolactone) triol (M.W. 900, 13 g) was dried under reduced pressure at 80° C. for 2 hours. It was cooled to room temperature, dissolved in 30 ml of dry toluene and then treated with ε-caprolactone (12 ml) and stannous octanoate (0.1 ml). The mixture was heated at 105° C. for 24 hours and then isocyanatoethyl methacrylate (6.85 ml) injected into the reaction at 60° C. The reaction mixture was heated at 60° C. for 24 hours and the product precipitated into petroleum ether.

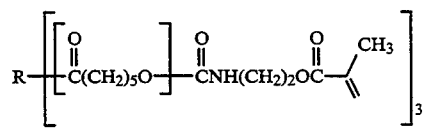

where R is poly(ε-caprolactone)triol.

The following examples are presented for a further understanding of the invention.

EXAMPLES

Crosslinking of Micelles

Method A

The polymer from I or IV (0.012 g) was dissolved in 50 ml acetone along with $6 \times 10^{-5}$ g of AIBN (2,2′-azobis(2-methyl propionitrile)) or benzoyl peroxide. To this was added 10 ml water and the miceliar aggregates formed by stripping off the acetone. The solution was deoxygenated and either UV irradiated for 8 hours or heated at 75° C. in a constant temperature bath for 16 hours. Instead of AIBN, ACVA (4,4′-azobis(4-cyanovaleric acid)) can also be used.

That crosslinking had occurred in the core was evidenced by diluting the fixed miceliar dispersion with acetone or tetrahydrofuran (THF) (a good solvent for both blocks) so that the resulting mixture contained more than 75% by volume acetone or THF. Under these conditions the uncrosslinked micelies dissolved and lost their bluish appearance while the crosslinked one remained bluish. Further, thermal analysis by differential scanning calorimetry showed a significant decrease in the heat of fusion after fixation. The size of the chemically fixed micelies remained essentially the same indicating no intermicellar crosslinking..

Method B

Method B is the same as Method A except for the inclusion of 1 to 5% by weight of the polymer of a polyfunctional crosslinker as described in preparation A and B. Another such monomer that was used was ethylene dimethacrylate.

In methods A and B, an organic solvent such as toluene can be included in the composition to aid in miceliar stability prior to crosslinking. The organic solvent can be present in an amount of between about 20 and 40 percent by weight of the copolymer and preferrably between about 25 and 30 percent by weight.

Method C

This method is used to crosslink oleophilic components having trialkoxy silane end groups.

The micellar aggregates were prepared as described in Method A except for the inclusion of trialkyl silane. The pH of the aqueous phase was then adjusted to 5.0 with acetic acid and the micelles were allowed to stand for 5 days at room temperature until hydrolysis and condensation of the trialkoxy silane in the core occured. Chemically fixed micelles can be isolated by ultracentrifugation or by freeze drying at about $-5°$ C. in a conventional manner.

Table I below illustrates useful copolymers that, when crosslinked as indicated, form useful particles of the invention. The copolymers, micelle aggregates and crosslinking of the micelles were carried out in each case in preparations analogous to those described above.

TABLE I

Chemically Fixed Micelles of the Formula:

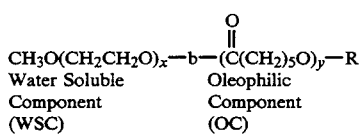

| Ex. | MW WSC | MW OC | R | Linking Method |
|---|---|---|---|---|
| 1 | 5K | 1K | H | Method A |
| 2 | 5K | 2K | H | Method A |
| 3 | 5K | 5K | H | Method A |
| 4 | 5K | 7K | H | Method A |
| 5 | 5K | 10K | H | Method A |
| 6 | 5K | 15K | H | Method A |
| 7 | 2K | 2K | H | Method A |
| 8 | 2K | 5K | H | Method A |
| 9 | 5K | 5K | $\underset{\text{CNHCH}_2\text{CH}_2-\text{O}-\text{C}}{\overset{\text{O}\quad\quad\quad\text{O}}{\|\quad\quad\quad\|}}\underset{\text{CH}_2\nearrow\;\text{CH}_3}{}$ | Method B |
| 10 | 5K | 2K | $\underset{\text{CH}_2}{\overset{\text{O}\;\;\;\text{CH}_3}{\|\;\;/}}\text{C}$ | Method B |
| 11 | 5K | 5K | $\underset{\text{CNH(CH}_2)_3\text{Si}-\text{OCH}_2\text{CH}_3}{\overset{\text{O}\quad\;\;\text{OCH}_2\text{CH}_3}{\|\quad\;\;\|}}\text{OCH}_2\text{CH}_3$ | Method C |
| 12 | 2K | 5K | R is H and OC contains 0.3K: <br> $+\text{CH}_2\text{CHO}+_z$ <br> \| <br> O <br> \| <br> C=O <br> / \ <br> CH$_2$ CH$_3$ | Method A |
| 13 | 2K | 0.5K | R is H and OC contains 0.1K: <br> $+\text{CH}_2\text{CHO}+_z$ <br> \| <br> CH$_2$ <br> \| <br> CH$_2$=CH | Method A |
| 14 | 5K | 5K | R is H and OC contains 0.3K: <br> $+\text{CH}_2\text{CHO}+_z$ <br> \| <br> O <br> \| <br> C=O <br> / \ <br> CH$_2$ CH$_3$ | Method A |

The chemically fixed copolymers of Examples 1, 2, 5, 7, 8, 10, 12 and 14 were isolated from the aqueous medium by either centrifugation followed by drying or by freeze drying at $-5°$ C.

Example 15

The polymer from preparation IV (0.01 g), AIBN (3% by weight with respect to the polymer), fluorescein (10% by weight with respect to the polymer) and 50 μl toluene were dissolved in 10 ml acetone. Water (10 ml) was added to this solution and the acetone was removed under reduced pressure. The resulting micelles with the incorporated fluorescein were fixed using UV radiation for two hours.

Example 16

Fluorescein containing a polymerizable group was prepared. Hydroxyethyl methacrylate (7.5 g) and fluorescein isothiocyanate (0.62 g) were stirred at room temperature in 3 ml of dimethyl formamide (DMF) in the presence of 1 μl of dibutyl tin dilaurate for 24 hours. The product was precipitated into ether and recovered.

The recovered product (0.018 g dissolved in 0.2 ml DMF) was dissolved along with the polymer from preparation IV (0.18 g) in 10 ml acetone along with toluene (0.1 g) and AIBN (0.005 g). To this was added 40 ml water, the acetone was removed and the composition was heated at 75° C. for 5 hours. The result was a chemically fixed micelle having chemically bound fluorescein in the core.

EXAMPLE 16

In vivo studies were conducted to determine the biological behavior of particles according to the invention. Rats were intravenously injected with the flourescently labeled particles ($1 \times 10^{12}$ particles per animal). After one hour, the animal was euthanized, the liver removed and processed for fluorimetry.

Two controls were prepared. One used poly(styrene) (PS) particles and the second used PS particles with a poly)ethylene oxide (PEO) based surfactant treatment known to improve the biocompatibility of polymer particles. A PEO-PCL chemically fixed particle of the invention (Example 12 above), having a flourescent dye associated with the core, was also tested. The results are given in the following table.

TABLE

| Particles | Biocompatibility | |
|---|---|---|
| | Size (nm) | % Liver Uptake |
| PS | 50 | 46 |
| PS + PEO | 50 | 7.6 |
| PEO — PCL (Invention) | 111 | 19 |

The results show that in spite of the fact that the particles of the invention were substantially larger than the control particles, they exhibited quite low liver uptake.

EXAMPLE 17

Enzymatic degradation of the chemically fixed PEO-PCL micelles (example 14 above) was followed in phosphate buffered saline using a pHstat by monitoring the carboxylic acid produced from the degradation of the caprolactone core. In 24 hours, at 37° C., the polymer core was degraded by a number of common lipases.

The invention has been described in detail with particular reference to preferred embodiments thereof, but it will be understood that variations and modifications can be effected within the spirit and scope of the invention.

We claim:

1. A composition comprising micelles that are composed of an amphiphilic block or graft copolymer comprising a water soluble component and an oleophilic component, wherein the micelles have been chemically fixed by crosslinking said oleophilic component while the micelles are in an aqueous environment, and wherein a drug is contained in the crosslinked oleophilic component of the copolymer.

2. A composition comprising a continuous phase having therein micelles wherein:
   a) the continuous phase is aqueous;
   b) the micelles are composed of an amphiphilic block or graft copolymer comprising a water soluble component and an oleophilic component; and
   c) the micelles have been chemically fixed by crosslinking the oleophilic component while the micelles are in said continuous phase.

3. A composition according to claim 1 or claim 2, wherein said water soluble component of the copolymer is a poly(alkylene oxide).

4. A composition according to claim 3 wherein said poly(alkylene oxide) is a poly(ethylene oxide).

5. A composition according to claim 1 or claim 2, wherein said oleophilic component of the copolymer is derived from monomers selected from the group consisting of caprolactone; propiolactone; β-butyrolactone; δ-valerolactone; ε-caprolactam; lactic acid; glycolic acid; hydroxybutyric acid; lysine, glutamic acid and derivatives thereof.

6. A composition according to claim 5 wherein said oleophilic component is functionalized with multifunctional monomers resulting in pendant crosslinkable groups.

7. A composition according to claim 6 wherein said multifunctional monomers are selected from the group consisting of allyl glycidyl ether; glycidyl methacrylate; and poly(cyanoacrylate).

8. A composition according to claim 1 or claim 2, wherein said oleophilic component of the copolymer is crosslinked with a polyfunctional acrylate or styrenic.

9. A composition according to claim 1 or claim 2, wherein the water soluble component and the oleophilic component of the copolymer are biocompatible and biodegradable.

10. A composition according to claim 1 or claim 2, wherein a drug is contained in the crosslinked oleophilic component of the copolymer.

11. A composition according to claim 1 or claim 2, wherein the molecular weight of the water soluble component of the copolymer is between about 1,000 and 50,000.

12. A composition according to claim 1 or claim 2, wherein the molecular weight of the oleophilic component of the copolymer is between 300 and 25,000.

13. A composition comprising micelles that are composed of an amphiphilic block or graft copolymer comprising a water soluble component and an oleophilic component, wherein the micelles have been chemically fixed by crosslinking said oleophilic component while the micelles are in an aqueous environment, and wherein said oleophilic component of the copolymer is derived from monomers selected from the group consisting of caprolactone; propiolactone; β-butyrolactone; δ-valerolactone; ε-caprolactam; lactic acid; glycolic acid; hydroxybutyric acid; lysine, glutamic acid and derivatives thereof.

14. A composition according to claim 13 wherein said oleophilic component is functionaiized with multifunctional monomers resulting in pendant crosslinkable groups.

15. A composition according to claim 14 wherein said multifunctional monomers are selected from the group consisting of allyl glycidyl ether; glycidyl methacrylate; and poly(cyanoacrylate).

* * * * *